(12) United States Patent
Haubrich

(10) Patent No.: US 6,379,300 B1
(45) Date of Patent: Apr. 30, 2002

(54) TELEMTRY SYSTEM FOR IMPLANTABLE MEDICAL DEVICES

(75) Inventor: Gregory J. Haubrich, Champlin, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/414,728

(22) Filed: Oct. 8, 1999

(51) Int. Cl.[7] .................................................. A61B 5/00
(52) U.S. Cl. ......................................................... 600/300
(58) Field of Search ................................ 600/300, 302, 600/308, 345, 360, 373, 374, 508, 509; 607/32, 33, 36, 60

(56) References Cited

U.S. PATENT DOCUMENTS

| | | |
|---|---|---|
| 4,233,985 A | 11/1980 | Hartlaub et al. |
| 4,542,532 A | 9/1985 | Mcuilkin |
| 5,107,833 A | 4/1992 | Barsness |
| 5,113,869 A | 5/1992 | Nappholz et al. |
| 5,127,404 A | 7/1992 | Wyborney et al. |
| 5,135,004 A | 8/1992 | Adams et al. |
| 5,331,966 A | 7/1994 | Bennett et al. |
| 5,350,411 A | 9/1994 | Ryan et al. |
| 5,360,437 A | 11/1994 | Thompson |
| 5,383,909 A | 1/1995 | Keimel |
| 5,387,228 A | 2/1995 | Shelton |
| 5,404,877 A | 4/1995 | Nolan et al. |
| 5,522,859 A | 6/1996 | Stroebel et al. |
| 5,522,862 A | 6/1996 | Testerman et al. |
| 5,683,432 A | 11/1997 | Goedeke et al. |
| 5,697,958 A | 12/1997 | Paul et al. |
| 5,720,770 A | 2/1998 | Nappholz et al. |
| 5,752,977 A | 5/1998 | Grevious et al. |
| 5,766,232 A | 6/1998 | Grevious et al. |
| 5,817,131 A | 10/1998 | Elsberry et al. |
| 5,861,019 A | 1/1999 | Sun et al. |
| 5,871,512 A | 2/1999 | Hemming et al. |
| 5,931,857 A | 8/1999 | Prieve et al. |

OTHER PUBLICATIONS

U.S. Patent Application SN 09/302,932, filed Apr. 30, 1999, Villaseca et al, entitled "Telemetry System for Implantable Medical Devices".

*Primary Examiner*—William E. Kamm
(74) *Attorney, Agent, or Firm*—Girma Wolde-Michael

(57) ABSTRACT

An implantable device having a hermetic housing containing a transceiver, circuitry for sensing a physiologic parameter or delivering a stimulus signal, an antenna mounted external to the hermetic enclosure, a medical lead, located external to the hermetic enclosure and a feedthrough extending through the wall of the hermetic enclosure. The antenna and the electrical lead are coupled to the feedthrough exterior to the device housing and the transceiver and the sensing or stimulating circuitry are coupled to the feedthrough internal to the device housing. The device is provided with a diplexer including high and low pass filters arranged to prevent passage of high frequency signals from the antenna to the sensing or stimulating circuitry and to prevent passage of low frequency signals from the medical lead to the transceiver.

10 Claims, 3 Drawing Sheets

TELEMTRY SYSTEM FOR IMPLANTABLE MEDICAL DEVICES

BACKGROUND OF THE INVENTION

This invention relates generally to the implantable medical devices and more specifically to telemetry systems for allowing communication between implanted medical devices and external programmers or monitors.

In the context of implantable medical devices, it has become common to provide a communication link between the implanted device and an external programmer or monitor in order to allow for transmission of commands from the external device to the implanted device and to allow for transmission of stored information and/or sensed physiological parameters from the implanted device to the external programmer. Conventionally, communication between an implanted device and an external programmer has been accomplished by means of a telemetry system which includes a transceiver located within the implanted medical device and an external programmer or monitor, each having a radio transmitter/receiver and one or more antennas.

The implanted device typically includes an antenna located either within the hermetic device housing containing the circuitry, as disclosed in U.S. Pat. No. 4,542,532 issued to McQuilkin, in a plastic header or connector block used to interconnect the device to electrical leads as disclosed in U.S. Pat. No. 5,697,958 issued to Patrick et al. or mounted to the device housing as in U.S. Pat. No. 5,861,019 issued to Sun et al. and U.S. Pat. No. 5,720,770 issued to Nappholz et al., all incorporated herein in their entireties. The programmer or monitor typically includes or consists of a programming head containing an antenna, intended to be placed on the patient's body in close proximity to the implanted device. The programming head may be coupled to the external programmer or monitor by means of a cord, as disclosed in U.S. Pat. No. 5.766,232 issued to Grevious et al.

More recently it has been proposed to provide communication systems for implantable devices in which the programming head is done away with, and communication occurs directly between the programmer or monitor, which may be located some distance from the patient, and the implanted medical device. Such systems are disclosed in U.S. Pat. No. 5,404,877 issued to Nolan et al, and U.S. Pat. No. 5,113,869 issued to Nappholz. In the Nappholz patent, in particular, the use of an electrical lead as the antenna for broadcasting RF signals to the programmer or monitor which may be located some feet away from the patient is suggested.

SUMMARY OF THE INVENTION

The present invention is directed toward a telemetry system for an implantable device which, like the devices in the above cited Sun et al., Patrick et al., Nolan and Nappholz patents in which the antenna is located external to the hermetic housing of the implantable device.

The antenna of the implanted device may take the form of a monopole antenna located external to the hermetic enclosure of the implanted device, having a length tuned to function optimally at the radio frequencies chosen for use in the telemetry system. The antenna itself may, for example, correspond to any of the implantable device antennas illustrated in commonly assigned co-pending U.S. patent application Ser. No. 09/302,932, filed Apr. 30, 1999 by Villaseca et al. for a "Telemetry System for Implantable Medical Devices", incorporated herein by reference in its entirety. Alternatively, the antenna may correspond to any of the antennas described in the above-cited Sun et a., Nappholz, Nolan or Patrick et al. patents cited above.

Implantable stimulators or monitors employing electrodes or other sensors and employing antennas located external to the device housing have typically required a separate feedthrough to connect the antenna to the transceiver within the device housing, in addition to one or more feedthroughs to connect electrodes or sensors to the pulse generators and/or sensing circuitry within the device housing. The inventors of the present invention have developed a telemetry system in which the transceiver can share a feedthrough with a sensor or a stimulation or sensing electrode, reducing the total number of feedthroughs required for the device. In particular, the present invention provides a diplexer which separates the higher frequency signals employed by the telemetry system from the lower frequency signals employed by the stimulation or sensing circuitry within the device. The diplexer may include a first filter bank located within the device housing and a second filter bank located external to the device housing. In some embodiments of the invention, the inherent characteristics of the antenna and/or stimulation /sensing lead coupled to the feedthrough may serve to provide some of the required filtering.

DETAILED DESCRIPTION OF THE PREFERRED EMBODIMENTS

Figure 1:
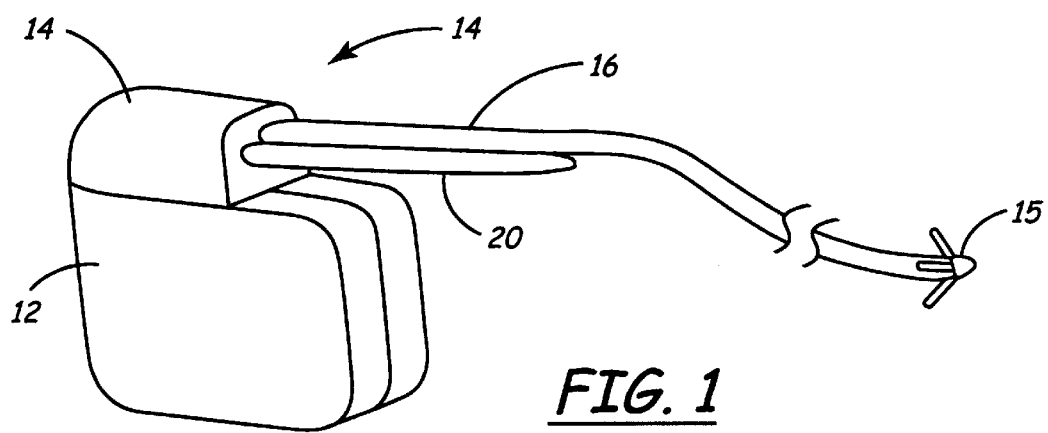
FIG. 1 is a drawing of an implantable cardiac stimulator of the sort in which the present invention may usefully be practiced.

FIG. 1 illustrates a cardiac pacemaker or other implantable stimulator in which the present invention may usefully be practiced. In the particular embodiment illustrated, the device 10 is provided with a hermetic metal enclosure 12 which contains the device circuitry and the power source. A sensing/stimulation lead 16 and a monopole antenna 20 are illustrated exiting from a connector block 14. Typically, the lead 16 is removably received in a bore within the connector block 14. Antenna 20 may be permanently affixed to the device, or may also be removably located in a second bore within the connector block 14. Antenna 20 may, for example, be a tuned monopole antenna of any of the sorts disclosed in the above cited application by Villaseca et al. Lead 16 may be a conventional monopolar cardiac pacing lead, wherein electrode 18 is used both for delivering stimulus pulses to the patient's heart and for sensing electrical signals indicative of depolarizations of the patient's heart.

The circuitry within device housing 12 includes a transceiver coupled to antenna 20 and pacing/sensing circuitry as is conventionally employed in implantable cardiac pacemakers and implantable pacemaker/cardioverter/ defibrillators, for example as disclosed in U.S. Pat. No. 5,871,512 issued to Hemming et al., U.S. Pat. No. 4,233,985 issued to Hartlaub, U.S. Pat. No. 5,817,131 issued to Ellsberry et al., U.S. Pat. No. 5,383,909 issued to Keimel et al., U.S. Pat. No. 5,360,437 issued to Thompson, U.S. Pat. No. 5,387,228 issued to Shelton or U.S. Pat. No. 5,522,859 issued to Stroebel et al. The transceiver circuitry may, for example, correspond to that described in the cited Villaseca et al. application or may correspond to other transceiver circuitry types, for example as disclosed in the above-cited patents or U.S. Pat. No. 5,752,977 issued to Grevious et al., U.S. Pat. No. 5,127,404 issued to Wyborny et al., U.S. Pat. No. 5,350,411 issued to Ryan et al, U.S. Pat. No. 5,107,833 issued to Barsness et al., U.S. Pat. No. 5,683,432 issued to Goedeke et al or U.S. Pat. No. 5,861,019 issued to Sun et al. While an RF telemetry systems are generally the norm as practiced in implantable medical devices, as reflected by the references cited above, if the frequency content of the telemetry system is high enough, the present invention may also be useful in systems employing conducted current, inductively coupled or capacitively coupled telemetry systems employing antennas external to the device housing.

It should also be understood that the invention may also usefully be practiced in other forms of implantable devices having leads which include stimulation electrodes, sensing electrodes or other types of physiologic sensors, for use in stimulating a patient's body tissue and/or monitoring physiological parameters within the patient's body. For example, the present invention may also be usefully applied in the context of implantable programmable neurostimulators, for example as disclosed in U.S. Pat. No. 5,817,131 issued to Ellsberry et al, or U.S. Pat. No. 5,522,862 issued to Testerman et al., implantable cardioverter/defibrillators as disclosed in U.S. Pat. No. 5,383,909 issued to Keimel et al. or U.S. Pat. No. 5,931,857 issued to Prieve et al. and implantable monitors as disclosed in U.S. Pat. No. 5,331,966 issued to Klein et al., or U.S. Pat. No. 5,135,004 issued to Adams et al., all incorporated herein by reference in their entireties. In this context, it should also be understood that the form of external antenna 20 employed by the device and the form of the lead carrying stimulation electrodes, sensing electrodes or other physiological sensor will vary substantially from product to product. Nonetheless, the present invention is believed useful in all of these contexts.

Figure 2:
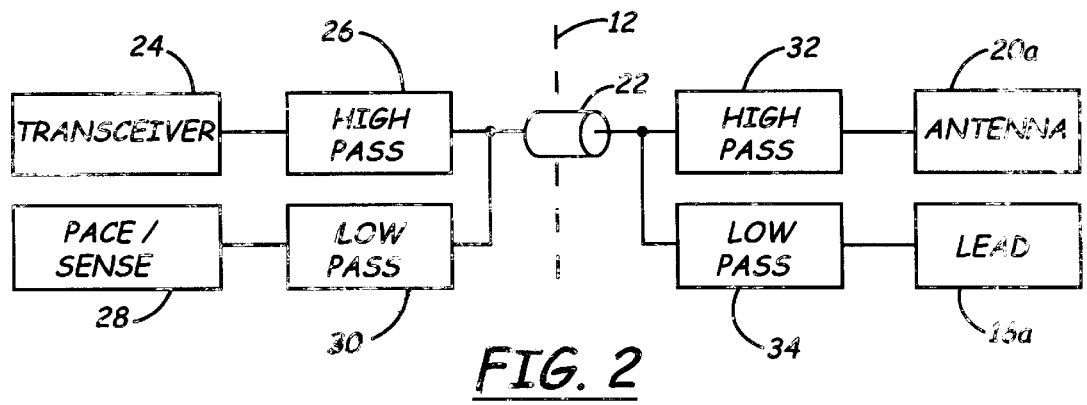
FIG. 2 is a block functional diagram of an implantable stimulator as illustrated in FIG. 1, employing the present invention.

FIG. 2 is a block functional diagram illustrating the organization of an implantable pacemaker in which the present invention is practiced. As illustrated, broken line 12 corresponds to the wall of the hermetic housing 12 illustrated in FIG. 1, with feedthrough 22 extending through the housing in a conventional fashion. In devices as illustrated in FIG. 1, feedthrough 22 would be located on the surface of the device housing 12 to which the connector module 14 is mounted, and the feedthrough wire extending through feedthrough 22 will be coupled, by means of the filter bank provided, to both the antenna 20a and lead 16a of the device, while that portion of the feedthrough wire extending internal to device housing 12 will be coupled by means of the internal filter bank to the transceiver 24 and pacing/sensing circuitry 28 of the device.

As illustrated, the diplexer according to the present invention includes high pass and low pass filtering circuitry 32 and 34 located external to the device housing 12 and corresponding high pass and low pass filtering circuitry 26 and 30 located internal to the device housing. High pass filter 32 serves to prevent the lower frequency signals associated with stimulus pulses or sensor control signals passed through feedthrough 22 from being applied to antenna 20. Low pass filter 34 prevents the high frequency signals generated by transceiver 24 from passing through to the lead 16a. Correspondingly, high pass filter 26 located internal to the device prevents low frequency signals from the lead 16a, for example, due to natural cardiac depolarizations or to the output of a physiologic sensor, from passing through to the input of transceiver 24 while low pass filter 30 prevents high frequency signals received by antenna 20a from passing into the pace/sense circuitry 28. The filter characteristics of the high and low pass filters employed must of course be chosen as a function of the respective frequency bands employed by the transceiver 24 and the pace/sense circuitry 28. In the context of a cardiac pacemaker, it is typical that the frequency content of the generated pacing pulses and the sensed cardiac electrogram signals fall in a range generally below 200 Hz, while the frequency range for the telemetry system is often 10 KHz or above and may be in the MHz range. In any case, the high pass and low pass filter characteristics must be chosen to be transparent to the signals of interest passing therethrough while simultaneously presenting a sufficiently high input impedance with regard to the signals not of interest to avoid distortion or corruption of the signals of interest.

Figure 3:
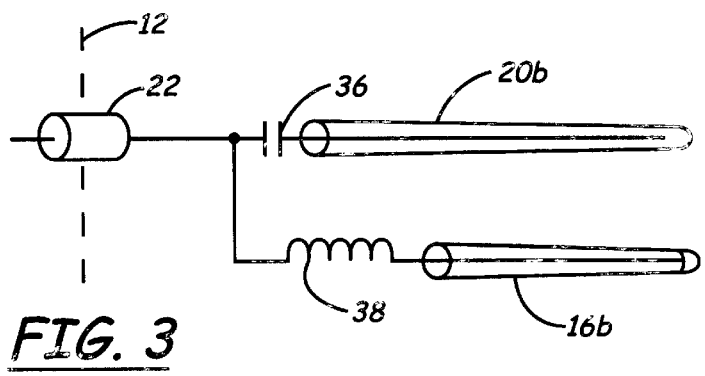
FIG. 3 is an illustration of one embodiment of that portion of the diplexer of the present invention located external to the device housing.
Figure 4:
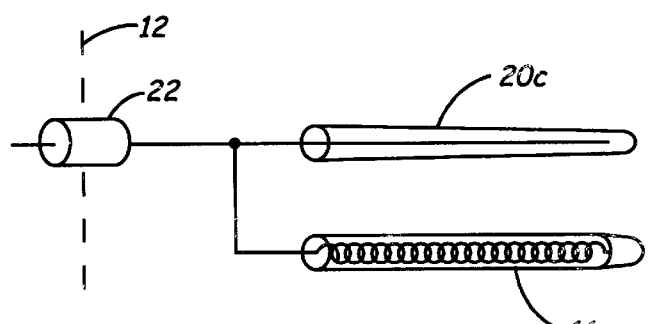
FIG. 4 illustrates an alternative embodiment of that portion of the diplexer located external to the device housing, in which inherent characteristics of the lead and antenna are relied upon to provide the required filtering.

FIG. 3 illustrates a first embodiment of the external portion of the diplexer according to the present invention. In this case, dotted line 12 also illustrates the enclosure 12 of the device, through which feedthrough 22 passes. In this case, the antenna 20b comprises a length of stranded wire surrounded by an insulating material, for example corresponding to the antennas described in the above-cited Villaseca et al application. In this case, the high pass filter portion of the diplexer may be performed by a small coupling capacitor 36, while the low pass filter function of the diplexer may be provided by means of a helically wound inductor 38. Alternatively, if the frequency ranges and physical construction of the lead and/or antenna permits, one or both of the separate filtering components (e.g. capacitor 36 and inductor 38) may be omitted. For example, in circumstances in which the carrier frequency of the telemetry system is sufficiently high, e.g. 50 MHz, the inherent inductance of a helically wound conductor coil within the lead may serve to provide the required low pass filtration, preventing the higher frequency telemetry signals generated by the transceiver from being passed down the lead. Similarly, in the event that the antenna, has a sufficiently small inherent capacitance, for example, taking the form of a short length of stranded conductor covered by an insulating sleeve, the relatively small capacitance of the antenna itself may serve to provide the required low pass filtration. Such a configuration is illustrated in FIG. 4, in which the device housing is illustrated at 12, the feedthrough is illustrated at 22 and the stub antenna 20c and pacing lead carrying a coiled conductor 16c are both illustrated as coupled directly to the wire through feedthrough 22.

Figure 5:
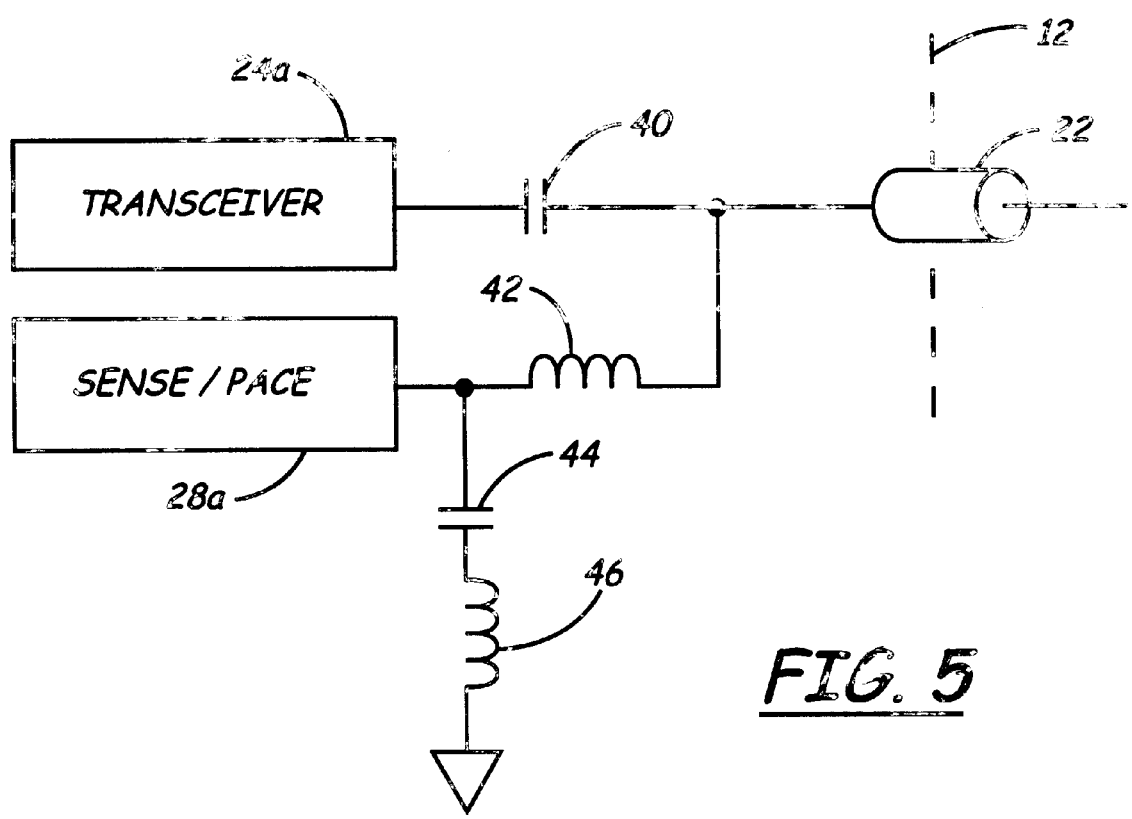
FIG. 5 is a functional schematic of one embodiment of a diplexer according to the present invention, illustrating that portion of the diplexer located within the device housing.

FIG. 5 illustrates one exemplary embodiment of the internal portion of the diplexer of the present invention, located within the device housing. As in FIGS. 2, 3 and 4, the device housing is illustrated by broken line 12 and the feedthrough is illustrated at 22. In this particular embodiment, the filter bank comprises a filter capacitor 40, an inductor 42, and an optional associated capacitor 44. Parasitic inductance of the circuitry, if present, is illustrated schematically at 46. Other filter circuits may be substituted. As illustrated, the diplexer provides a high pass filter for preventing signals received from the lead from being provided to the transceiver 24a and prevents high frequency signals received by the antenna from being applied to sensing/pacing circuitry 28a. The values of capacitor 40, capacitor 44 and inductor 42 must of course be optimized depending upon the relative frequency ranges of the telemetry system and the signals to be received from the lead. However, in the context of a telemetry system operating in the frequency range of 400 MHz, in which the sensing/pacing circuitry 28 is intended to receive cardiac signals and to deliver cardiac pacing pulses, capacitor 40 may be, for example, 33 picoFarads inductor 42 may be, for example 0.33 microHenries, capacitor 44 may be, for example 150 picoFarads with parasitic inductance 46 assumed to be approximately 1 nanoHenry. Specific values and configurations of the required low and high pass filters for both the internal and external portions of the diplexer, may of course, be readily determined as a function of the frequency components of the respective signals to be blocked from and/or passed to the transceiver, pacing/sensing circuitry, lead and antenna.

In conjunction with the above application, I claim:

1. In an implantable device comprising a hermetic housing containing a transceiver, circuitry for sensing a physiologic parameter, an antenna mounted external to the hermetic enclosure, and a medical lead, located external to the hermetic enclosure and a feedthrough extending through the wall of the hermetic enclosure, the improvement wherein;

said antenna and said electrical lead are coupled to said feedthrough exterior to said device housing and said transceiver and said sensing circuitry are coupled to said feedthrough internal to said device housing; and wherein said device further comprises a diplexer comprising high and low pass filters arranged to prevent passage of high frequency signals from said antenna to said sensing circuitry and to prevent passage of low frequency signals from said medical lead to said transceiver.

2. A device according to claim 1 wherein the high pass filter comprises a filter capacitor.

3. A device according to claim 1 or 2, wherein said lead comprises means for sensing a physiologic parameter.

4. A device according to claim 3, wherein said means for sensing a physiologic parameter comprises an electrode.

5. A device according to claim 1 wherein the low pass filter comprises an inductor.

6. In an implantable device comprising a hermetic housing containing a transceiver, circuitry for sensing a physiologic parameter, an antenna mounted external to the hermetic enclosure, and a medical lead, located external to the hermetic enclosure and a feedthrough extending through the wall of the hermetic enclosure, the improvement wherein;

said antenna and said electrical lead are coupled to said feedthrough exterior to said device housing and said transceiver and said sensing circuitry are coupled to said feedthrough internal to said device housing; and wherein said device further comprises a diplexer comprising high and low pass filter means for preventing passage of high frequency signals from said transceiver down said lead and for preventing passage of low frequency signals from said lead to said transceiver.

7. A device according to claim 6 wherein the lead comprises a coiled conductor and wherein the low pass filtering means comprises said coiled conductor.

8. A device according to claim 6 wherein the antenna comprises a tuned monopole antenna having a capacitance and wherein the high pass filtering means comprises the effective capacitance of the antenna.

9. A device according to claim 6 wherein the high pass filtering means comprises a filter capacitor.

10. A device according to claim 6 wherein the low pass filtering means comprises an inductor.

* * * * *